US00PP22567P2

(12) United States Plant Patent
Jansen

(10) Patent No.: US PP22,567 P2
(45) Date of Patent: Mar. 6, 2012

(54) ***PENSTEMON* PLANT NAMED 'GRAPE TAFFY'**

(50) Latin Name: ***Penstemon* spp.**
Varietal Denomination: Grape Taffy

(75) Inventor: Robert D. Jansen, Beaverton, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/927,577

(22) Filed: Nov. 17, 2010

(51) Int. Cl.
*A01H 5/00* (2006.01)

(52) U.S. Cl. ..... Plt./465

(58) Field of Classification Search ..... Plt./465
See application file for complete search history.

*Primary Examiner* — Annette Para
(74) *Attorney, Agent, or Firm* — Jondle & Associates, P.C.

(57) ABSTRACT

A new and distinct cultivar of *Penstemon* plant characterized by large purple red flowers with white throats, dense flower clusters, long bloom time, a compact, upright, well branched habit, with multiple crown from the base, clean-looking, deep green, attractive foliage, and excellent vigor.

1 Drawing Sheet

Botanical denomination: *Penstemon* spp.
Variety designation: 'Grape Taffy'.

BACKGROUND OF THE INVENTION

The present invention relates to a new and distinct cultivar of *Penstemon*, given the name, 'Grape Taffy'. *Penstemon* is in the family Scrophulariaceae. This plant originated from an open pollinated cross using *Penstemon* 'Violet Kissed', an unpatented plant, as the seed parent. This cultivar was selected for its compact growing habit, large flowers in dense clusters, long flowering time, vigor, and clean attractive look. It is an ideal plant for a sunny border in full sun.

Compared to the seed parent, *Penstemon* 'Violet Kissed', an unpatented plant, the new cultivar has red purple lips rather than violet. Both have a white throat.

Compared to *Penstemon* 'Wine Kissed', an unpatented plant, the new cultivar has red purple lips rather than dark wine red. Both have a white throat.

*Penstemon* 'Grape Taffy' is uniquely distinguished by its:

1. large purple red flowers with white throats;
2. dense flower clusters;
3. long bloom time;
4. compact, upright, well branched habit, with multiple crown from the bas;
5. clean-looking, deep green, attractive foliage; and
6. excellent vigor.

The new variety has been reproduced only by asexual propagation (cuttings and micropropagation). Each of the progeny exhibits identical characteristics to the original plant. Asexual propagation by cuttings and micropropagation using terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a close up of a one year old *Penstemon* 'Grape Taffy' in the summer in Canby, Oreg.

FIG. 2, foreground, shows a two year old *Penstemon* 'Grape Taffy' in bloom growing in full sun in the trail bed in July in Canby, Oreg.

DETAILED PLANT DESCRIPTION

The following is a detailed description of the new *Penstemon* cultivar based on observations of one-year-old specimens grown outside in one gallon pots in Canby, Oreg. in late July. The color descriptions are all based on The Royal Horticultural Society Colour Chart, 5$^{th}$ edition.

Plant:

*Type*.—Herbaceous perennial.
*Form*.—Upright, branching.
*Cold Hardiness*.—USDA Zone 7-10.
*Size*.—Grows to 26 cm wide and 58 cm high.
*Vigor*.—Excellent.
*Stem number*.—3 stems from the crown.
*Stem*.—Upright, grows to 44 cm long and 4 mm wide (at the base), glabrous, internodes grow to 3.5 cm long, Yellow Green 146C.
*Rooting*.—Plants root easily from stem cuttings.

Leaf:

*Type*.—Simple.
*Arrangement*.—Opposite.
*Shape*.—Lanceolate.
*Venation*.—Pinnate.
*Margins*.—Entire.
*Apex*.—Acuminate.
*Base*.—Sessile.
*Blade size*.—Grows to 11 cm long and 3.5 cm wide.
*Surface texture*.—Glabrous on both sides.
*Leaf color*.—Topside Green 137A, bottom side Green 137B.

Inflorescence:

*Type*.—Terminal, many flowered, dense thyrse.
*Number of flowers per inflorescence*.—26 on average.
*Size of inflorescence*.—Grows to 16 cm long and 9 cm wide.
*Peduncle*.—Grows to 2.5 cm long and 1 mm wide, glabrous, Yellow Green 146D.

*Pedicel*.—Grows to 17 cm long and 4 mm wide, pubescent, Yellow Green 146D.

*Bloom period*.—June through September in Canby, Oreg. if spent blooms are removed.

Flower bud:

*Size*.—2 cm long and 12 mm wide.

*Description*.—Ovoid, bulging, flattened ventrically.

*Color*.—Purple N77B except Greyed Green 193C on bottom tube.

Flower:

*Type*.—Zygomorphic, perfect.

*Shape*.—Tubular, bilabiate.

*Size*.—Grows to 4 cm long and 4.5 cm wide.

*Corolla description*.—Grows to 4 cm long and 4.5 cm wide; tube is funnel-form in the calyx for 4 mm long and 6 mm wide, inflating for 25 mm long to 24 mm wide, flaring into 5 lobes, the two smaller top lobes flare back (15 mm wide and 12 mm deep) and two larger lateral lobes flare out (20 mm wide and 17 mm deep), and the lower lobe flares down (16 mm wide and 12 mm deep), lobe margins entire, tips obtuse; outside glandular, inside glabrous; outside Red Purple 70A maturing to Purple Violet N81B except bottom side where it lightens to White NN155B at tube base; inside color is Red Purple N78A on lobes, tube is White NN155D with bee tracks of Red Purple N78A.

*Calyx description*.—10 mm deep and 13 mm wide, 5 overlapping lobes cut to the base, each lobe broadly ovate in shape, 10 mm deep and 7 mm wide, margins entire, tip acute, base cuneate, Yellow Green 145A and pubescent inside and outside.

*Pistil description*.—1, 28 mm long, ovary 6 mm long and 2.5 mm wide, Yellow Green 145A; style 22 mm long and less than 1 mm wide, Red Purple 70A on the bottom half to Violet Blue 91C on the top half.

*Stamen description*.—5, one sterile without an anther, held within the corolla, filaments 3 cm long and White NN155C, anthers 3 mm wide and 1.5 deep, Greyed Purple N186A, pollen White 155A.

*Fragrance*.—None.

*Lastingness*.—A flower lasts 5 to 6 days.

Fruit:

*Type*.—Capsule.

*Fertility*.—Good.

*Size*.—1.2 cm deep and 4 mm wide.

*Color*.—Brown 200A to B.

Seed:

*Shape*.—Irregular.

*Size*.—2 mm long.

*Color*.—Brown 200A.

Pests and diseases:

Excellent disease tolerance to root rot, a common problem for *Penstemon*. Leaf spot, rust, and powdery mildew may be a problem, but have not been observed on the new cultivar. No known disease or pest resistances.

I claim:

1. A new and distinct cultivar of *Penstemon* plant substantially as shown and described.

* * * * *

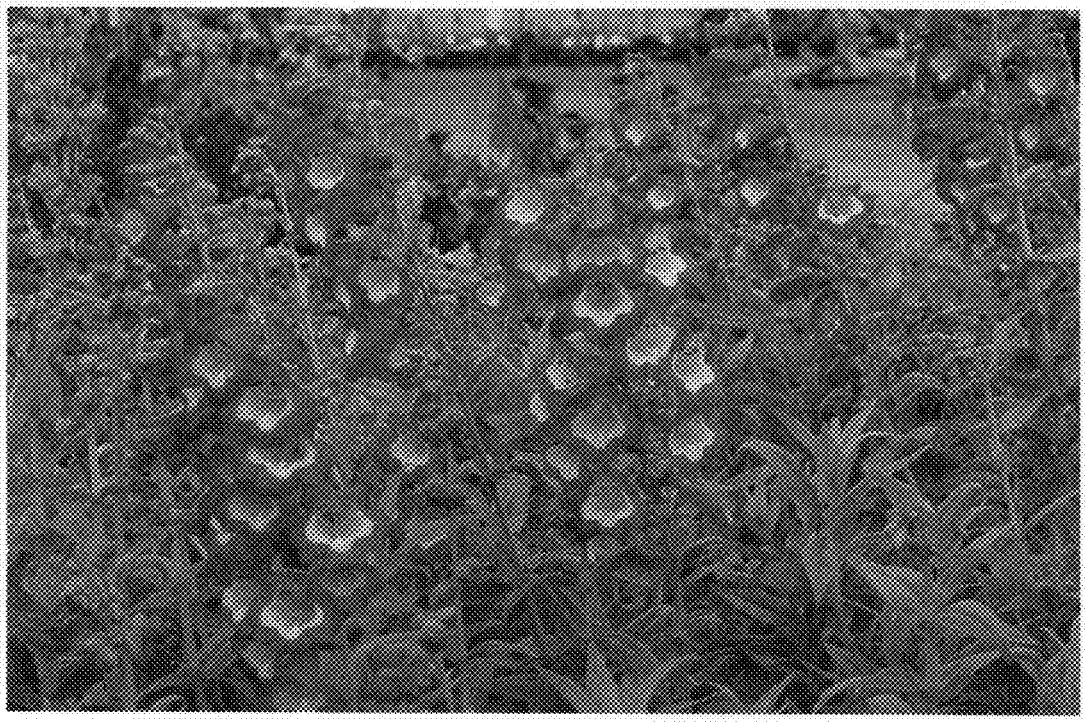

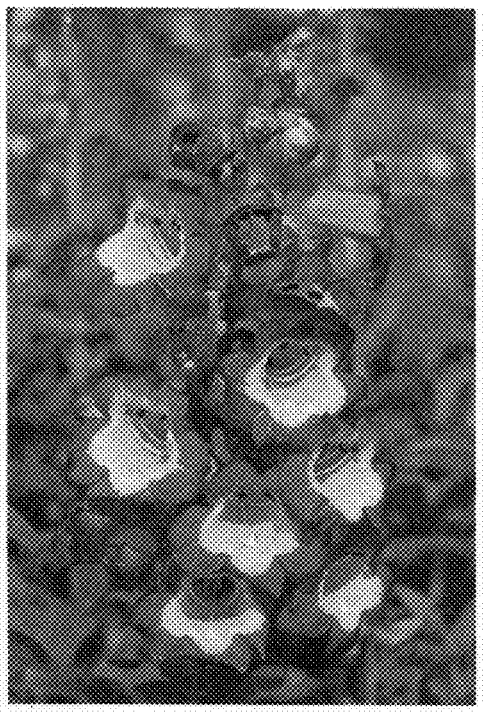
Figure 1 to left
Figure 2 below